United States Patent [19]
El-Mallawany et al.

[11] Patent Number: 5,304,203
[45] Date of Patent: Apr. 19, 1994

[54] TISSUE EXTRACTING FORCEPS FOR LAPAROSCOPIC SURGERY

[75] Inventors: Amin El-Mallawany, Pepper Pike; Jan J. Lewandowski, South Euclid, both of Ohio

[73] Assignee: NuMed Technologies, Inc., Independence, Ohio

[21] Appl. No.: 963,718

[22] Filed: Oct. 20, 1992

[51] Int. Cl.⁵ .............................................. A61B 17/28
[52] U.S. Cl. .................................... 606/207; 606/205; 606/206; 606/170; 128/751
[58] Field of Search .............................. 128/749–754; 606/1, 45, 51, 52, 110, 113, 116, 138, 139, 140, 142, 144, 170, 205–211

[56] References Cited

U.S. PATENT DOCUMENTS

| | | | |
|---|---|---|---|
| 2,668,538 | 2/1954 | Baker | 606/207 |
| 2,723,666 | 11/1955 | Greenberg | 606/205 |
| 4,246,698 | 1/1981 | Lasner et al. | 30/134 |
| 4,271,838 | 6/1981 | Lasner et al. | |
| 4,753,235 | 6/1988 | Hasson | |
| 4,753,238 | 6/1988 | Galser | |
| 4,760,848 | 8/1988 | Hasson | 606/206 |
| 4,819,633 | 4/1989 | Bauer et al. | 606/52 |
| 4,944,741 | 7/1990 | Hasson | 606/206 |
| 4,955,897 | 9/1990 | Ship | 606/210 |
| 4,977,900 | 12/1990 | Fehlinge et al. | 128/751 |
| 5,100,420 | 3/1992 | Green et al. | 606/143 |
| 5,133,713 | 7/1992 | Huang et al. | 606/46 |
| 5,133,735 | 7/1992 | Slater et al. | 606/205 |
| 5,133,736 | 7/1992 | Bales, Jr. et al. | 606/205 |
| 5,139,487 | 8/1992 | Baber | 604/165 |
| 5,141,519 | 8/1992 | Smith et al. | 606/205 |
| 5,171,258 | 12/1992 | Bales et al. | 128/751 |
| 5,201,752 | 4/1993 | Brown et al. | 128/751 |
| 5,201,759 | 4/1993 | Ferzli | 128/751 |
| 5,209,747 | 5/1993 | Knoepfler | 606/52 |

FOREIGN PATENT DOCUMENTS 2346401 3/1974 Fed. Rep. of Germany ...... 606/206

*Primary Examiner*—Stephen C. Pellegrino
*Assistant Examiner*—Glenn Dawson
*Attorney, Agent, or Firm*—Jon L. Roberts; Thomas M. Champagne

[57] ABSTRACT

Tissue extracting forceps are disclosed which have been designed for use in laparoscopic surgery. The forceps firmly grasp tissue or organs which are to be moved or removed during the procedure. The grasping members of the forceps are aligned such that fragmentation damage to the grasped tissue is minimized. The mechanical layout of the forceps allows the user to manipulate the working end for a distance, so that the user's fingers do not get in the way of the surgical procedure. The working end of the forceps is adaptable to be used with grasping members of different shapes, or with disposable cutting instruments. Any of these working ends may be incorporated in the same overall mechanical design.

12 Claims, 9 Drawing Sheets

TISSUE EXTRACTING FORCEPS FOR LAPAROSCOPIC SURGERY

FIELD OF THE INVENTION

The present invention relates generally to surgical instruments of the forceps type, used for grasping and extracting body tissue or organs (such as cysts or tumors) during laparoscopic surgical procedures. More specifically, the invention relates to forceps-type surgical instruments that may be worked by the user at a point that is not immediately proximate to the forceps jaws, allowing for remote manipulation of the grasped tissue.

DESCRIPTION OF RELATED ART

During laparoscopic procedures a trocar, or sharp tipped stylus, is inserted into the patient's abdomen. The trocar is inserted into the abdomen while enclosed in a tubular sheath or cannula. Once the required incision has been made by the trocar, it is removed from the sheath, which remains in the patient as a trans-abdominal passage. This passage can be used for insertion of surgical instruments such as that of the instant invention.

Devices currently exist which can be used during such surgical procedures. U.S. Pat. No. 4,955,897 to Ship discloses tissue forceps to be used during surgery. The forceps have sharp, directly opposing teeth for grasping the tissue. A surgeon using these forceps must be able to have his hands immediately proximate to the tissue being grasped.

U.S. Pat. No. 4,753,235 to Hasson discloses a surgical forceps instrument having a locking device to keep the forceps closed on the grasped tissue. Again, the surgeon's hands must be close to the surgical area in order to use the forceps.

U.S. Pat. No. 4,944,741 to Hasson discloses a complicated design for a forceps device for laparoscopic surgery. This device has many parts and a large spring element controlling the motion of the forceps jaws.

U.S. Pat. No. 4,753,238 to Galser discloses a manifold and adapter device for use with a catheter.

All of the above instruments are single purpose instruments. If other procedures or tissues are encountered, a different instrument must be used.

SUMMARY OF THE INVENTION

The instant invention improves upon previous devices by providing a novel design that is easy to operate, yet is more versatile for many different types of extracting. The laparoscopic forceps of the present invention may be reconfigured and utilized without changing the same basic forceps design.

The invention incorporates an easy to use scissors grip which is used to manipulate the surgical instrument end. The instrument end is a jaw type design, consisting of a pair of symmetrical pivoting arms. The tissue grasping surface of the pivoting arms may assume a number of shapes depending upon the tissue to be extracted. The preferred embodiment is furnished with two rows of separated teeth. Each tooth has the shape of a truncated cone with a square base (i.e., a pyramid). On each arm there are two parallel rows of teeth. The teeth rows are positioned to alternate such that the teeth from first row face gaps created between teeth of the second row and vice versa. The number of teeth and the rows of teeth may vary in position so long as the upper and lower teeth are alternate to one another. The scissors grip may be equipped with a locking mechanism or may be spring loaded in order to keep the grasping jaws in a closed position.

It is therefore an object of the present invention to provide an improved surgical instrument of the forceps type for laparoscopic and general endoscopic surgery, assuring firm and reliable tissue grasping capability yet preventing tissue fragmentation.

It is yet another object of the present invention to provide such a surgical instrument that has a simple design and is easy to operate.

It is still another object of the present invention to provide a versatile surgical instrument which can be easily reconfigured to provide different working ends without changing the basic design.

These and other objects and advantages of the present invention will be made apparent in the following detailed description of the invention and in the attached claims.

BRIEF DESCRIPTION OF THE DRAWINGS

The invention is described in more detail in the following section, with reference to the following drawings.

DETAILED DESCRIPTION OF THE INVENTION

Figure 1:
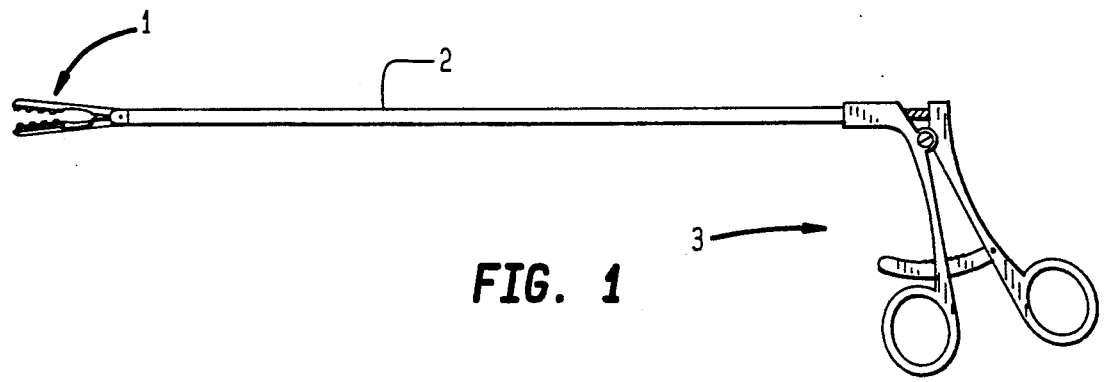
FIG. 1 is a complete view of the extracting tissue forceps for laparoscopic surgery.

FIG. 1 shows the tissue extracting forceps of the present invention. The forceps comprise a distal portion 1, an intermediate portion 2 and a proximal portion 3.

Figure 2:
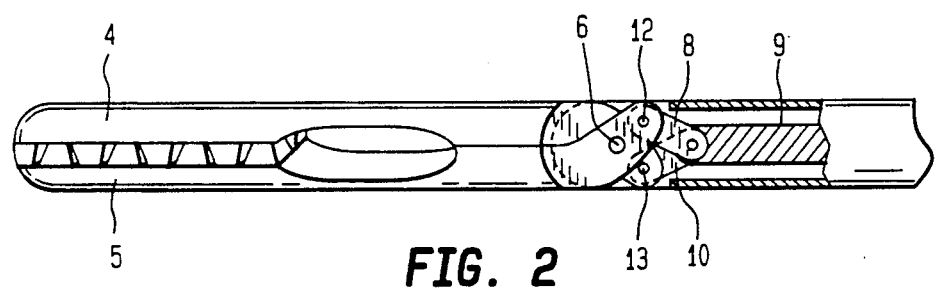
FIG. 2 is a section view of the grasping jaws with the actuating mechanism in a closed position.
Figure 3:
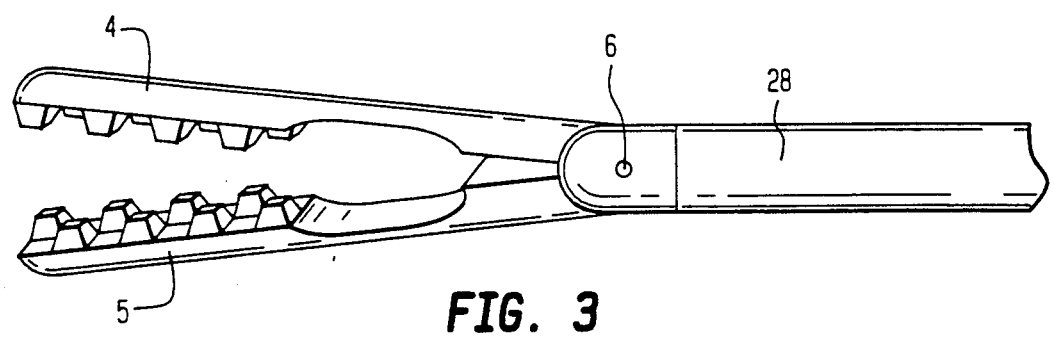
FIG. 3 is a view of the grasping jaws in the open position.

Referring to FIG. 2, the distal portion 1, that is, the end that is introduced to the patient's body during surgery is shown. This distal portion 1 consist of a pair of pivotally moving, grasping jaw-type arms 4 and 5 with a lever mechanism made of link plates 8 and 10 supported with pivot pins 12 and 13. (See also FIGS. 3 and 4).

Referring to FIG. 2, the intermediate portion 2 is made of rigid tubing 28 holding an actuating rod 9.

Figure 7:
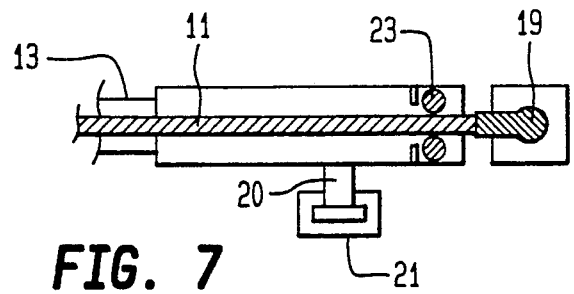
FIG. 7 is a top view of the proximal portion of the instrument showing the flushing port, O-ring assembly and mechanical coupling element.
Figure 8:
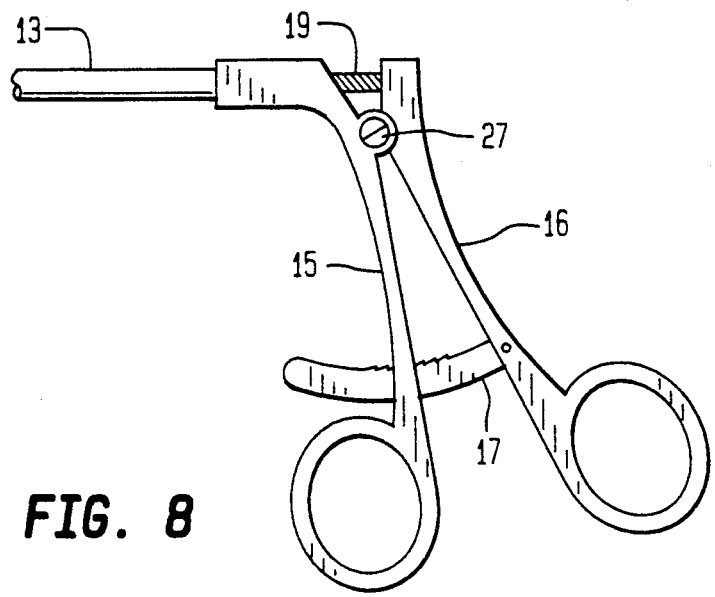
FIG. 8 shows the actuating handle assembly with a locking mechanism.
Figure 9:
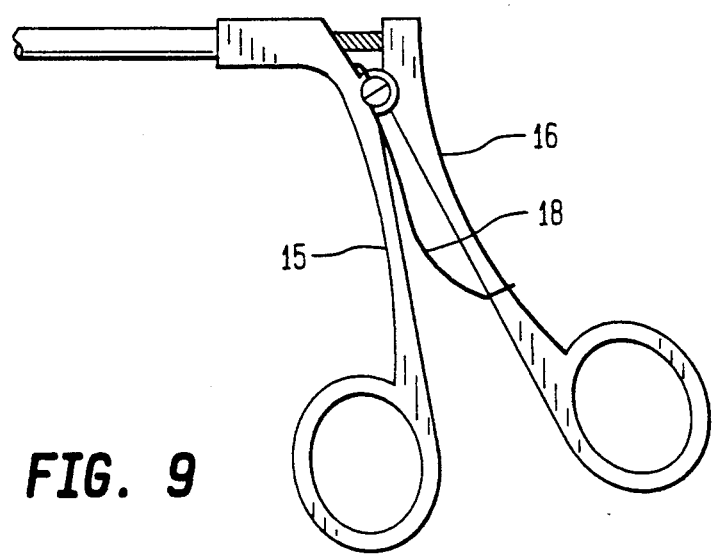
FIG. 9 shows a spring biased actuating handle assembly.

Referring to FIG. 8, the proximal portion 3, that is, the end that is manipulated by the user is shown. This proximal portion 3 consists of an actuating scissors grip handle utilizing a flushing port 20, and air tight O-ring assembly 23, and a locking mechanism 17 or spring biased mechanism. See also FIGS. 7 and 9.

In the preferred embodiment, the jaws are designed to provide a tight and stable grasp on tissue or of an organ which is to be removed, and to simultaneously prevent tissue fragmentation.

Figure 4:
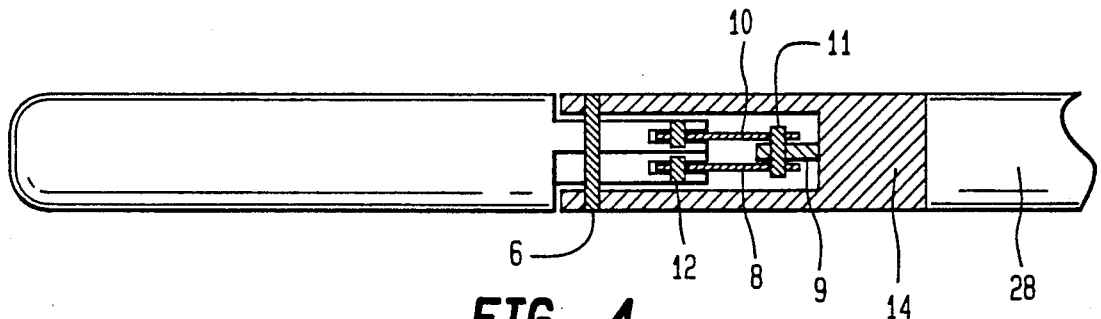
FIG. 4 is a top view of the grasping jaws actuating mechanism.
Figure 5:
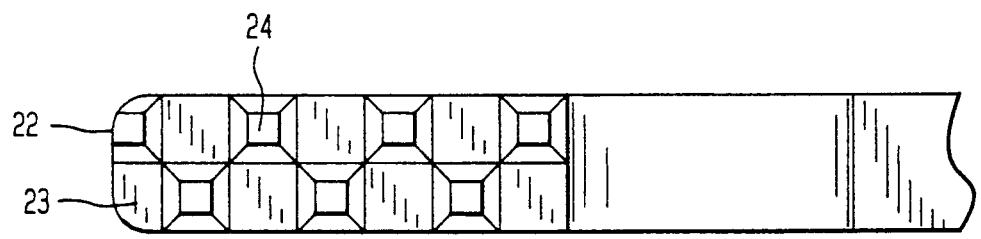
FIG. 5 is a view of the tissue grasping surface with pyramidal teeth located on the grasping element (grasping jaw).
Figure 6:
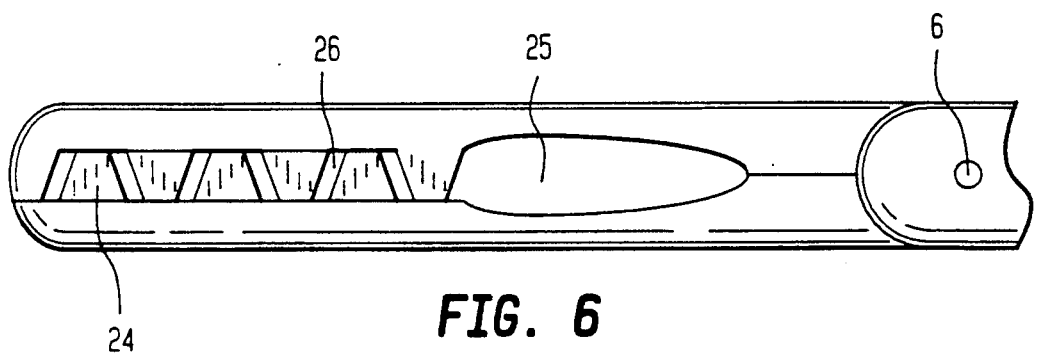
FIG. 6 is a side view of the grasping elements (grasping jaw) in the closed position.

The jaw consists of two symmetrical, pivoting arms 4 and 5 connected by a pivot pin 6. A top view of one of the pivot arms is shown in FIG. 4. The pivot pin 6 allows for the opening and closing movement of the arms 4 and 5. The tissue grasping capability is provided by the specifically designed grasping surface. In the preferred embodiment, the tissue grasping surface of each pivoting (FIGS. 5 and 6) is equipped with two rows of teeth 22 and 23. Each tooth 24 has the shape of a truncated cone with a square base. In the preferred embodiment, there are two parallel rows of teeth on each arm. The teeth rows are positioned alternately such that the teeth from the first row face gaps between the teeth of the second row and vice versa. The middle portion of each arm 4 and 5 is recessed so that in the closed position a pocket 25 is created to accommodate the grasped tissue as shown in FIG. 6. When the jaws are in the closed position, the teeth located on the first arm fit into the gaps between the teeth located on the second arm. The distance between teeth (gaps) are larger than the teeth. In effect, in the closed position a space 26 is created, accommodating grasped tissue and protecting the tissue against cutting (fragmentation) by the teeth. This unique positioning of the teeth on the grasping jaws assures firm grasping of the tissue with minimal damage, allowing for safe removal of large chunks of extracted tissue.

The forceps's arms 4 and 5 are opened and closed by the motion of the actuating rod 9. The linear motion of the actuating rod 9 is transferred to the pivoting motion of the arms 4 and 5 through a pair of coupling link plates 8 and 10. The link plates 8 and 10 are attached at one end to the actuating rod 9 with pivot pin 11. The other end of each link plate 8 and 10 is attached to the forceps arm 4 and 5 through two pivot pins 12 and 13, located on the unattached sides of the arms 4 and 5, opposite the two rows of grasping teeth 22 and 23.

The intermediate portion 2 of the laparoscopic forceps consists of the rigid tubing 28 holding the actuating rod 9 which slides freely inside of the tubing 28. A fork sleeve 14 is attached to the distal end of the tubing 28, as shown in FIG. 4. This fork sleeve 14 provides support for the pivoting arms 4 and 5.

The proximal portion 3 of the instrument includes scissors grip actuating handles 15 and 16. The proximal portion 3 also includes a coupling element 19, a flushing port 20, and a protective cap 21.

The handle comprises two elements. Handle element 15 is immovably attached to the rigid tubing 28. The handle element 16 is pivotally coupled to handle element 15 by set screw 27. Both elements 15 and 16 have loops at the ends for insertion of the user's fingers. The actuating rod 9 is coupled with movable handle element 16 by means of a ball shaped coupling element 19 attached to the proximal end of the actuating rod 9. The coupling element 19 is inserted into a receptacle On the upper portion of handle element 16.

The O-ring assembly 23 assures an airtight fit between the actuating rod 9 and the rigid tubing 28, as required in laparoscopic procedures. Flushing port 20 is provided for the draining of any fluid which may collect in tubing 28 during the course of the surgical procedure and for the cleaning of the instrument.

The scissors grip actuating handles may be equipped with a locking/releasing mechanism 17 or spring biasing mechanism 18 in order to keep the grasping jaws in a closed position.

Figure 10:
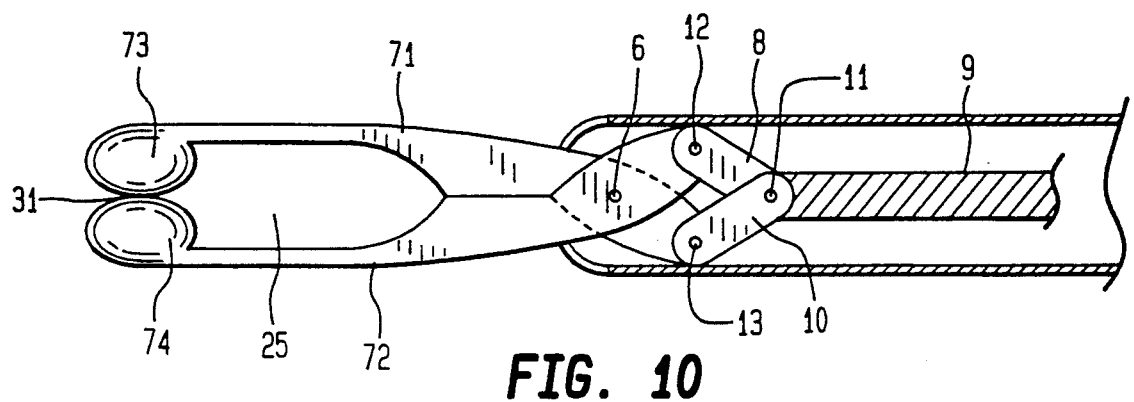
FIG. 10 shows a section view of the grasping jaws terminating in elliptically shaped prongs, in a closed position.
Figure 11:
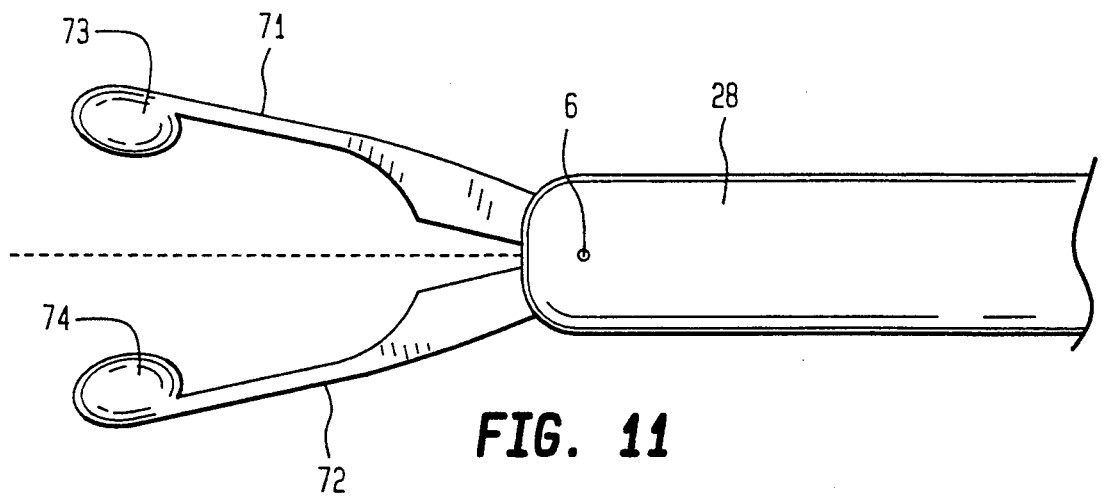
FIG. 11 is a view of the grasping jaws terminating in elliptically shaped prongs, in an open position.

In alternate embodiments, the tissue grasping surface can assume any of a number of shapes. FIGS. 10 and 11 show such a shape. The pivoting arms 71 and 72 in this embodiment terminate in elliptically shaped tips 73 and 74. When the jaws are in the closed position, the tips touch, holding the grasped tissue firmly at grasping surface 31. The relative thinness of pivoting arms in the vicinity of the tips creates a gap to accommodate the grasped tissue, protecting the tissue against fragmentation.

Figure 12:
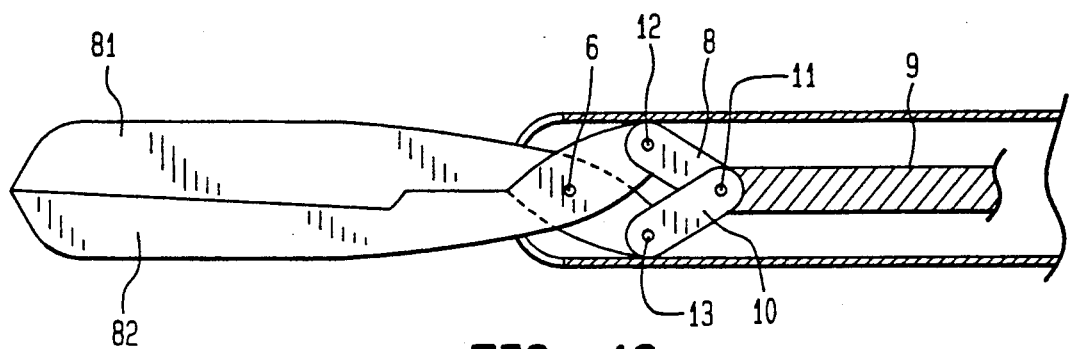
FIG. 12 shows a section view of the grasping jaws terminating in cutting arms, in a closed position.
Figure 13:
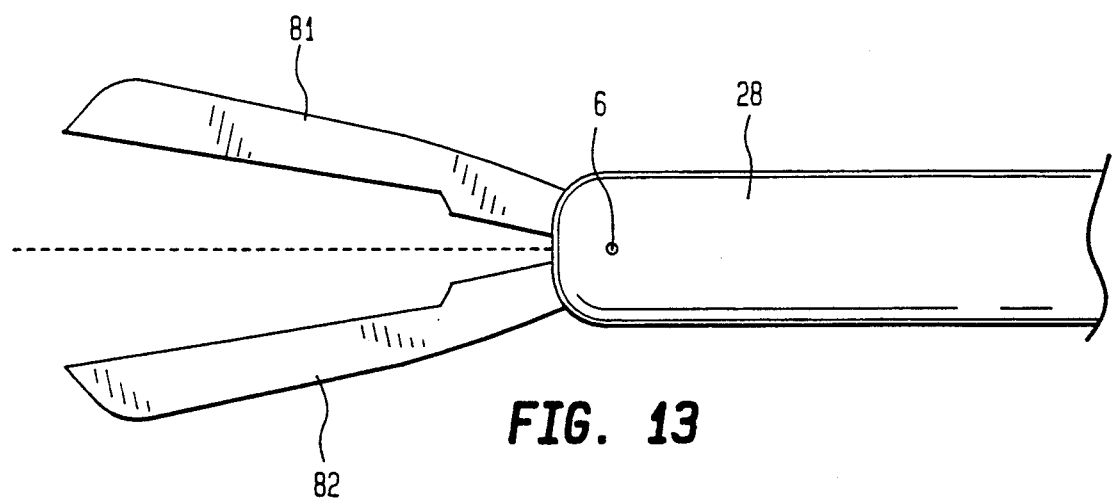
FIG. 13 is a view of the grasping jaws terminating in cutting arms, in an open position.

In some circumstances, the user of the present invention may wish to cut tissue rather than grasp it. The pivoting arms 81 and 82 may terminate in cutting arms rather than prehensile implements. The user may then cut the tissue without putting his hands immediately proximate to the area to be cut. As shown in FIGS. 12 and 13, this embodiment of the invention only requires modification of the pivoting arms 81 and 82. The distal end of the activating rod 9 may also be adapted such that whichever embodiment of the pivoting arms is used may be quickly and easily removed and replaced. This is an especially important feature when the cutting arm embodiment is in use. During surgery, cutting surfaces do not remain sufficiently sharp with repeated use and must be replaced frequently during a particular procedure.

Figure 14:
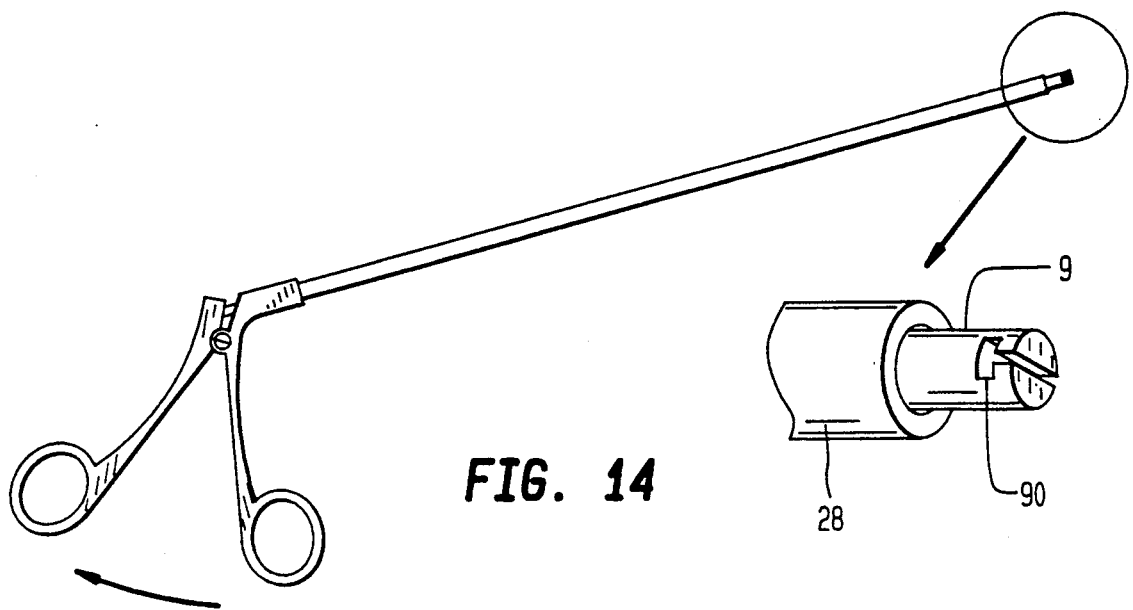
FIG. 14 shows the distal end of the actuating rod with the removable forceps removed.
Figure 15:
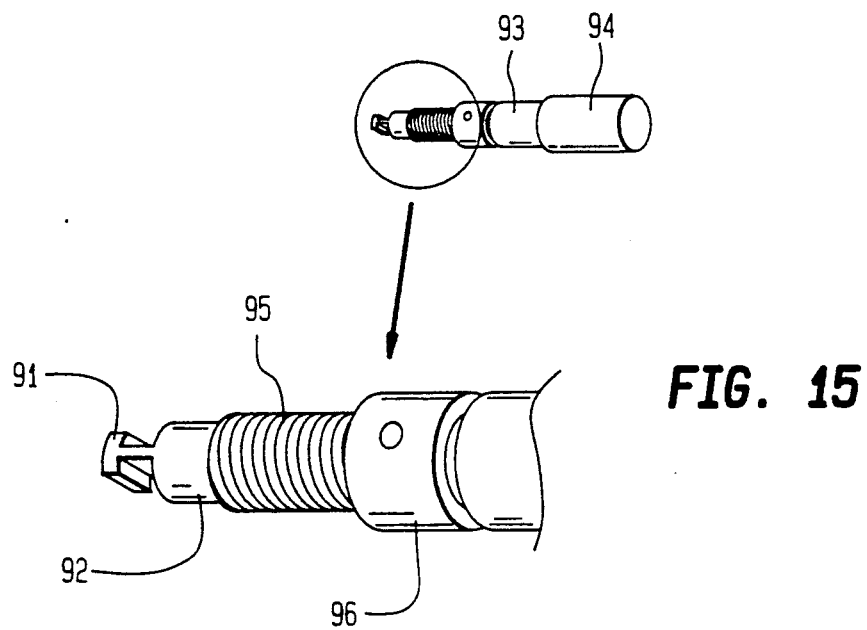
FIG. 15 shows a coupling prong on the removable forceps.

As shown in FIG. 14, the actuating rod 9 may terminate at the distal end with a coupling notch 90, which is in this example T-shaped. The coupling notch 90 should be shaped to mate with the coupling prong 91, seen in FIG. 15. Coupling prong 91 is located on one end of actuating rod extension 92, which forms a part of the disposable tip of this embodiment. The other end of the actuating rod extension 92 terminates in the cutting arm embodiment described previously. The cutting arm embodiment is enclosed within a rigid tubing extension 93 and a protective blade cover 94. The rigid tubing extension 93 outer surface has screw threads 95, to mate with screw threads on the inside surface of the distal end of the rigid tubing 28.

Figure 16:
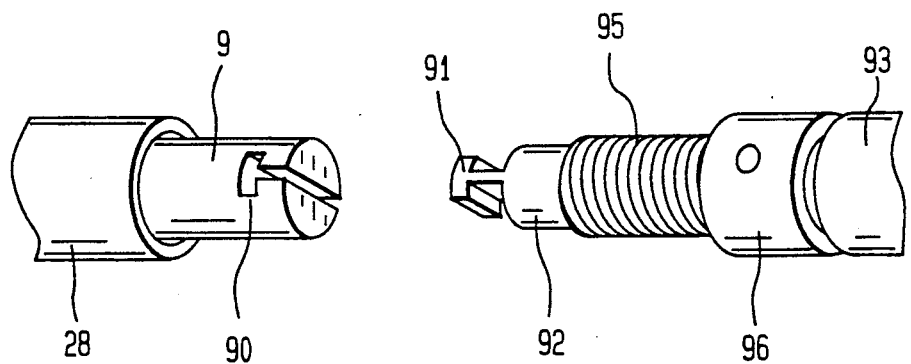
FIG. 16 shows the coupling prong next to the coupling notch.
Figure 17:
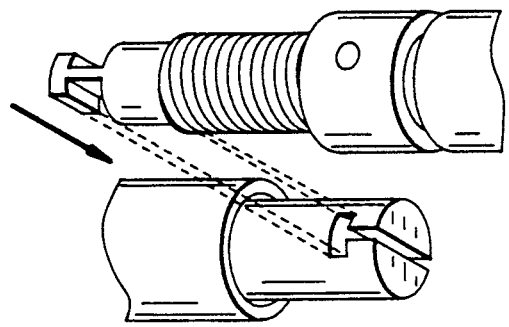
FIG. 17 shows the coupling prong aligned for mating with the coupling notch.
Figure 18:
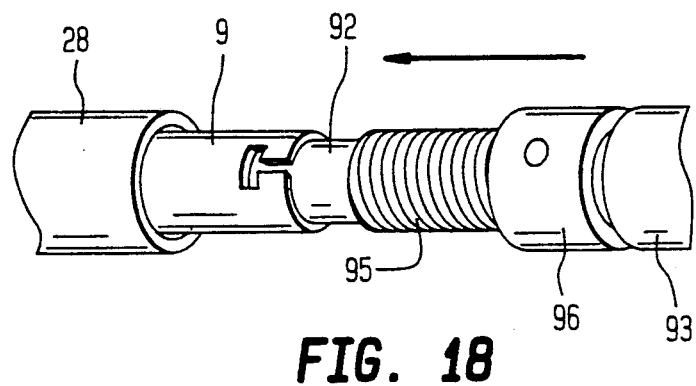
FIG. 18 shows the mated coupling prong and coupling notch.
Figure 19:
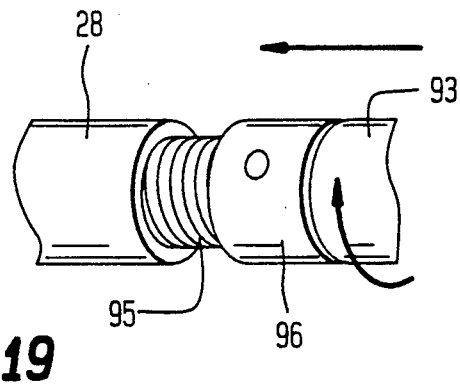
FIG. 19 shows the removable forceps engaging screw threads on the rigid tubing.
Figure 20:
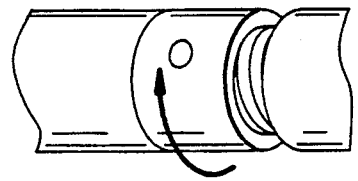
FIG. 20 shows a lock-nut being turned to secure engagement of the removable forceps.
Figure 21:
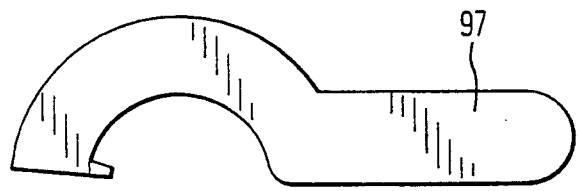
FIG. 21 a wrench for tightening the lock-nut.
Figure 22:
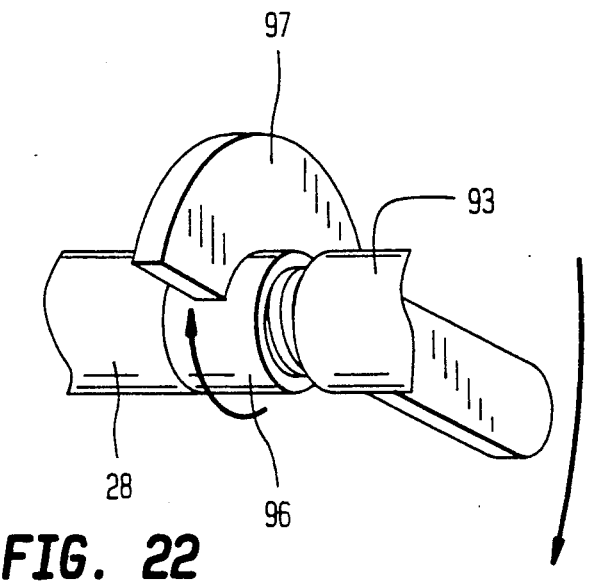
FIG. 22 shows the lock-nut being further tightened with a wrench.

To attach the disposable arm embodiment, the handle side of the device is first aligned with the blade side, as shown in FIG. 16. The coupling prong 91 is then inserted into the coupling notch 90, as shown in FIG. 17. Once connected in this manner, the rigid tubing extension 93 may be slid over the distal end of the actuating rod 9 (FIG. 18), where the rigid tubing screw threads 95 may be engaged by rotating the disposable blade side (FIG. 19). When the tip is in place and has the correct orientation relative to the handle end, the safety lock-nut 96 may be turned in order to secure the engagement (FIG. 20). The safety lock-nut 96 may be further tightened by using a small wrench 97 (FIGS. 21 and 22). The protective blade cover 94 may then be removed and the blade embodiment can be sterilized and put to use.

Figure 23:
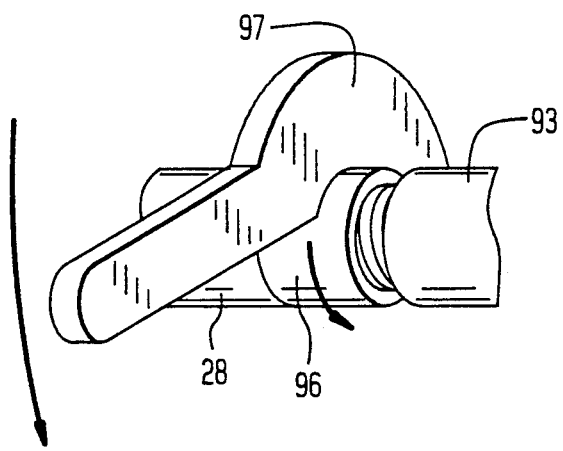
FIG. 23 shows the lock-nut being loosened with a wrench.
Figure 24:
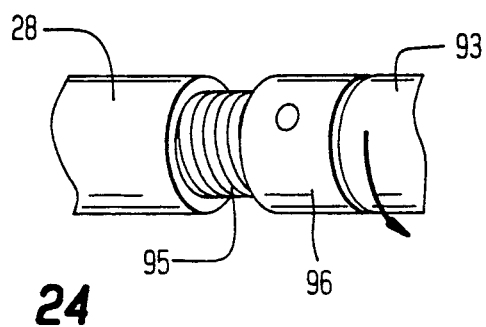
FIG. 24 shows a lock-nut being turned to loosen engagement of the removable forceps.
Figure 25:
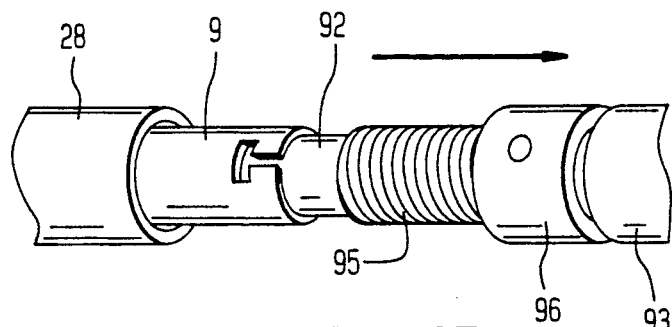
FIG. 25 shows the removable forceps being disengaged from screw threads on the rigid tubing.
Figure 26:
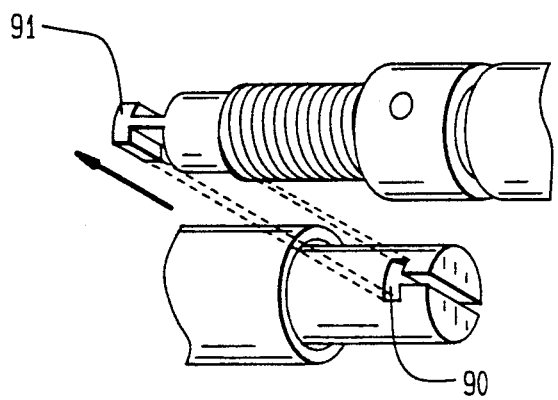
FIG. 26 shows the coupling prong and the coupling notch pulled apart.

To remove the blade end for disposal, the previous steps are merely executed in reverse. A wrench 97 may be used to loosen the lock-nut 96, as shown in FIG. 23. The blade end may then be rotated to disengage the screw threads 95 (FIG. 24), and the rigid tubing extension 93 may be slid back (FIG. 25). Once the coupling prong 91 and coupling notch 90 are disengaged, as shown in FIG. 26, the blade end may be thrown away and the handle may be reused with a new disposable tip.

Preferred and alternative embodiments have now been described in detail. It is to be noted, however, that these descriptions are merely illustrative of the principles underlying the inventive concept. It is therefore contemplated that various modifications of the disclosed embodiments will, without departing from the spirit and scope of the present invention, be apparent to those skilled in the art.

We claim:

1. A surgical instrument for laparoscopic procedures comprising:

a distal portion, an intermediate portion, and a proximal portion;

the distal portion comprising first and second pivotally connected arms connected at one end to a lever means, the first and second pivotally connected arms also having unattached ends with opposing faces;

the intermediate portion comprising an actuating rod having a distal end and a proximal end and a rigid tube having a distal tip and a proximal tip, the actuating rod being slidably located inside the rigid tube;

the proximal portion comprising first and second handle means;

the distal end of the actuating rod being connected to the lever means;

the first handle means immovably connected to the rigid tube;

the second handle means pivotally coupled to the proximal end of the actuating rod;

the first handle means pivotally connected to the second handle means;

the first and second handle means operable to remotely cause the unattached ends of the first and second pivotally connected arms to move angularly toward and away from each other into closed and opened positions; and the surgical instrument further comprising a rigid tubing extension having a distal tip and a proximal tip, the proximal tip of said rigid tubing extension being removably engaged to the distal tip of the rigid tube; and an actuating rod extension for connecting the distal end of the actuating rod to the lever means, the actuating rod extension having a proximal tip and a distal tip;

the distal end of the actuating rod being removably engaged with the proximal tip of the actuating rod extension.

2. The surgical instrument according to claim 1 wherein the first and second pivotally connected arms having a plurality of rows of alternately positioned teeth in the shape of square based truncated cones located on the unattached ends of the arms.

3. The surgical instrument according to claim 2 wherein the teeth located on the first arm fit into gaps between the teeth located on the second arm when the arms are in a closed position.

4. The surgical instrument according to claim 3 wherein space is created between the teeth located on the first arm and the teeth located on the second arm when the arms are in a closed position, due to the gaps between the teeth being larger than the teeth that fit into the gaps.

5. The surgical instrument according to claim 1 wherein a recess between the first and second pivotally connected arms exists when the unattached ends of the first and second arms are touching.

6. The surgical instrument according to claim 1 wherein the first handle means is further attached to the second handle means by a ratchet means to lock the first and second handle means into desired relative positions.

7. The surgical instrument according to claim 1 wherein the first handle means is further attached to the second handle means by a spring means which, when uncompressed, operates to keep the first and second pivotally connected jaws in a fully closed position.

8. The surgical instrument according to claim 1 wherein the proximal portion includes a sealing means between the actuating rod and the rigid tube.

9. The surgical instrument according to claim 1 wherein the proximal portion includes a capped port in the first handle means for flushing and draining any accumulated fluid present in the rigid tube.

10. The surgical instrument according to claim 1 wherein the first and second pivotally connected arms have elliptically shaped prongs located on the unattached ends of the arms, the prongs touching when the arms are in a fully closed position.

11. The surgical instrument according to claim 1 wherein the opposing faces of the first and second pivotally connected arms have cutting edges forming a cutting means.

12. The surgical instrument according to claim 1 wherein the pivotally connected arms have a protective cover that is removably attached to the distal tip of the rigid tubing extension.

* * * * *